(12) United States Patent
Lee

(10) Patent No.: US 10,799,410 B2
(45) Date of Patent: Oct. 13, 2020

(54) EXCRETA DISPOSAL APPARATUS CUSTOMIZED TO HUMAN BODY

(71) Applicant: CURACO, INC., Seongnam-si, Gyeonggi-do (KR)

(72) Inventor: Hoonsang Lee, Seoul (KR)

(73) Assignee: CURACO, INC., Seongnam-si, Gyeonggi-do (KR)

( * ) Notice: Subject to any disclaimer, the term of this patent is extended or adjusted under 35 U.S.C. 154(b) by 0 days.

(21) Appl. No.: 15/548,133

(22) PCT Filed: Feb. 3, 2015

(86) PCT No.: PCT/KR2015/001114
§ 371 (c)(1),
(2) Date: Aug. 2, 2017

(87) PCT Pub. No.: WO2016/125925
PCT Pub. Date: Aug. 11, 2016

(65) Prior Publication Data
US 2018/0021196 A1 Jan. 25, 2018

(51) Int. Cl.
*A61G 9/02* (2006.01)
*A61F 5/442* (2006.01)
(Continued)

(52) U.S. Cl.
CPC .............. *A61G 9/003* (2013.01); *A47K 10/48* (2013.01); *A61F 5/442* (2013.01); *A61F 5/4408* (2013.01);
(Continued)

(58) Field of Classification Search
CPC . A61G 9/00; A61G 9/02; A61G 9/003; A61G 9/006; A61G 7/0005; A61F 5/449; A61F 5/4408; A61F 5/451
(Continued)

(56) References Cited

U.S. PATENT DOCUMENTS

| 371,193 A | * | 10/1887 | Haertel | A61G 9/003 4/450 |
| 849,472 A | * | 4/1907 | Gold | A61G 9/003 4/455 |

(Continued)

FOREIGN PATENT DOCUMENTS

JP 2003153931 A 5/2003
JP WO 2006046532 A1 * 5/2006 ............. A61F 5/451
(Continued)

OTHER PUBLICATIONS

Machine Translation for WO 2006046532 A1.*
(Continued)

*Primary Examiner* — Erin Deery
(74) *Attorney, Agent, or Firm* — Panitch Schwarze Belisario & Nadel LLP

(57) ABSTRACT

A excreta disposal apparatus is customized to a human body and includes a body having a seating unit, which has a shape corresponding to the curved shape of the genital area and buttocks of the human body and also has a disposal space open toward the genital area and buttocks of the human body so as to take excreta discharged from the human body. A main body unit, which is connected to the seating unit, is mountable between the legs of the human body and has a receiving space therein. A discharge channel is provided in the receiving space and communicates with the disposal space to discharge the excreta in the disposal space to the outside.

13 Claims, 10 Drawing Sheets

(51) Int. Cl.
*A61G 9/00* (2006.01)
*A61F 5/44* (2006.01)
*A61F 5/451* (2006.01)
*A47K 10/48* (2006.01)

(52) U.S. Cl.
CPC ............... *A61F 5/451* (2013.01); *A61G 9/00* (2013.01); *A61G 9/02* (2013.01)

(58) Field of Classification Search
USPC .............................. 4/450, 545, 455, 546, 447
See application file for complete search history.

(56) References Cited

U.S. PATENT DOCUMENTS

| | | | | |
|---|---|---|---|---|
| 1,758,236 | A | * | 5/1930 | Olson .................... A61G 9/006 4/144.4 |
| 5,681,297 | A | * | 10/1997 | Hashimoto ............. A61F 5/451 119/164 |
| 6,394,988 | B1 | * | 5/2002 | Hashimoto ............. A61F 13/84 604/327 |
| 2013/0158489 | A1 | * | 6/2013 | Ying ....................... A61F 5/451 604/355 |
| 2016/0136338 | A1 | * | 5/2016 | Lee .......................... A61M 3/06 604/319 |

FOREIGN PATENT DOCUMENTS

| | | | |
|---|---|---|---|
| JP | 3122883 U | | 6/2006 |
| KR | 200453814 Y1 | | 5/2011 |
| KR | 20120097946 A | | 9/2012 |
| KR | 20130055594 A | | 5/2013 |
| WO | WO-2014208814 A1 | * | 12/2014 ............... A61M 3/06 |

OTHER PUBLICATIONS

Machine Translation for JP200315931.*
Int'l Search Report dated Sep. 21, 2015 in Int'l Application No. PCT/KR2015/001115.

* cited by examiner

EXCRETA DISPOSAL APPARATUS CUSTOMIZED TO HUMAN BODY

CROSS-REFERENCE TO RELATED APPLICATION

This application is a Section 371 of International Application No. PCT/KR2015/001114, filed Feb. 3, 2015, which was published in the Korean language on Aug. 11, 2016, under International Publication No. WO 2016/125925 A1, the disclosure of which is incorporated herein by reference.

TECHNICAL FIELD

The present invention relates to an excreta disposal apparatus customized to a human body, and more particularly, to an excreta disposal apparatus customized to a human body including a seating unit corresponding to a curved shape of the genital area and buttocks of a user for the disposal of excreta.

BACKGROUND ART

In general, since the patients or the elderly, who have mobility difficulties or who are unable to move their lower body by their own will, do not have the ability to handle their own excreta, there is an inconvenience that a guardian or a caregiver should always reside at hand.

Therefore, in order to solve such an inconvenience, an excreta disposal apparatus for collecting excreta by directly contacting the body has been researched and developed. Such an excreta disposal apparatus is designed to receive and suck a user's excreta and discharge the excreta to the outside so that the excreta can be automatically treated even if the guardian or the caregiver does not reside around the user.

However, since the disposal apparatus is designed without considering the body of the user and is concentrated only on the function of the excreta disposal, the conventional excreta disposal apparatus developed to date has a problem that the usability is very low. Generally, since a part around the buttocks or the genital area where excreta is excreted is sharply curved, the excreta disposal apparatus is difficult to adhered, there are many cases where the excreta leaks out between the human body and the excreta disposal apparatus.

In addition, the users, such as the patients or the elderly, who use the excreta disposal apparatus often live in a bed and frequently cannot change their posture on their own. When such a state persists for a long time, a bedsore occurs, so it is necessary to periodically change the posture. However, since the posture cannot be changed in the state where the excreta disposal apparatus is worn, there is an inconvenience to remove the excreta disposal apparatus.

Therefore, a method for solving such problems is required.

DISCLOSURE

Technical Problem

The present invention has been made in view of the above problems, and provides an excreta disposal apparatus capable of preventing leakage of excreta while a user wears the excreta disposal apparatus, and improving the feelings of wearing.

The present invention also provides an excreta disposal apparatus which can be free from the limitation of the behavior even when the user wears the excreta disposal apparatus.

The problems of the present invention are not limited to the above-mentioned problems, and other problems not mentioned can be clearly understood by those skilled in the art from the following description.

Technical Solution

In an aspect, there is provided an excreta disposal apparatus customized to a human body, the apparatus including: a body comprising a seating unit, which has a shape corresponding to a curved shape of genital area and buttocks of the human body and also has a disposal space open toward the genital area and buttocks of the human body so as to take excreta discharged from the human body, and a main body unit, which is connected to the seating unit so as to be mounted between legs of the human body and has a receiving space therein; and a discharge channel, which is provided in the receiving space and communicates with the disposal space so as to discharge the excreta in the disposal space to the outside.

The disposal space includes an urine disposal unit corresponding to the genital area of the human body, and a feces disposal unit corresponding to a hip of a human body.

The excreta disposal apparatus further includes an extension portion extended from the seating unit and configured to contact the buttocks of the human body.

The extension portion is formed in such a manner that height decreases when progressing from a rear side to a front side.

The extension portion is formed in such a manner that height decreases when progressing from a center to the side.

The extension portion is formed in such a manner that a recessed groove is formed in a position corresponding to a coccyx of human body.

A width of an upper portion of the body is narrower than a width of a lower portion of the body.

A through hole is formed in a rear side of the main body unit so that an external connection pipe can be inserted into the receiving space.

A spraying portion which is exposed to the disposal space and sprays washing water.

The excreta disposal apparatus further includes a flow channel switching unit which is provided in the receiving space and supplies washing water introduced from the outside to the spraying portion.

The excreta disposal apparatus further includes an air blowing unit which is provided in the receiving space and blows dry air to the disposal space.

The excreta disposal apparatus further includes a detection sensor which is provided in the disposal space and senses an existing of excreta.

The excreta disposal apparatus further includes a pad detachably attached to surround a periphery of the seating unit.

The excreta disposal apparatus further includes a fastening member which is provided around the seating unit to be in close contact with a user's body, and each contact area has an inclination corresponding to a curvature inclination of a corresponding human body part.

The disposal space includes: an urine disposal unit corresponding to the genital area of the human body; and a feces disposal unit corresponding to the buttocks of the human body, wherein the fastening member is separately provided to the feces disposal unit and the urine disposal unit respectively.

The fastening member includes: a buttocks contact area which is in contact with user's buttocks; and a thigh contact area which is extended upward from both sides of the buttocks contact area and is in contact with the inside of user's thigh.

The buttocks contact area has a contact surface contacting the human body is inclined upwards in a direction in which the disposal space is formed.

The thigh contact area has a contact surface contacting the human body is inclined upwards in a direction in which the disposal space is formed.

The fastening member has an inclination of contact surface contacting the human body which decreases when progressing from the thigh contact area to the buttocks area.

The excreta disposal apparatus further includes a pad detachably attached to surround a periphery of the seating unit, wherein the body includes an extension portion which is extended from the seating unit and is configured to contact the buttocks of the human body, and wherein the fastening member is formed to be stepped from a rear side of the extension portion by a height corresponding to a thickness of the pad.

Advantageous Effects

In order to solve the above-described problems, the present invention provides an excreta disposal apparatus customized to a human body having the following effects.

First, since the seating unit is formed to correspond to the curved shape of the genital area and buttocks of a user and can be adhered to the user's body, there is an advantage that the leakage of the excreta can be prevented in a state where the user wears the excreta disposal apparatus.

Secondly, since the main body unit also has a size corresponding to the width between the legs of the user, there is an advantage that the posture of the user can be maintained naturally.

Third, there is an advantage that the user's feelings of wearing is greatly improved.

Fourth, there is an advantage that the user is not restricted in the behavior even when the user wears the excreta disposal apparatus, and the posture can be freely changed.

The effects of the present invention are not limited to the effects mentioned above, and other effects not mentioned can be clearly understood by those skilled in the art from the description of the claims.

MODE FOR INVENTION

Figure 1:
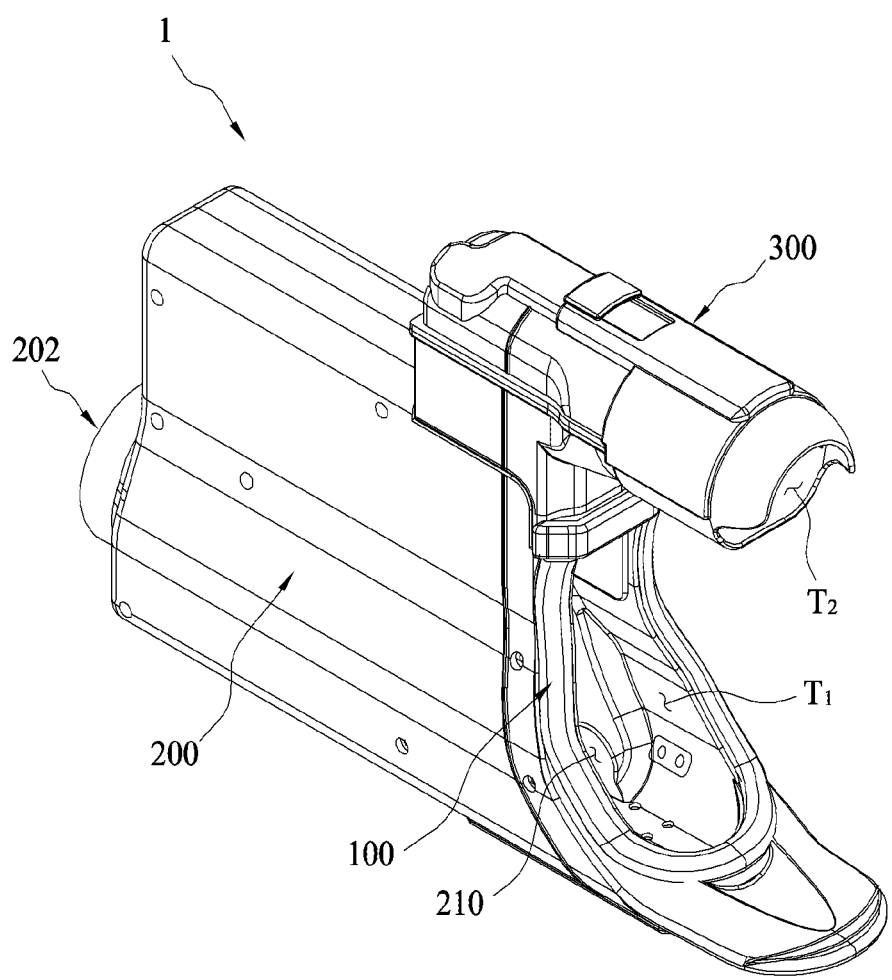
FIG. 1 is a perspective view showing an entire structure of an excreta disposal apparatus according to an embodiment of the present invention.

Hereinafter, preferred embodiments of the present invention will be described with reference to the accompanying drawings. In describing the present embodiment, the same designations and the same reference numerals are used for the same components, and further description thereof will be omitted.

FIG. 1 is a perspective view showing an entire structure of an excreta disposal apparatus 1 according to an embodiment of the present invention.

As shown in FIG. 1, the excreta disposal apparatus 1 according to an embodiment of the present invention includes a body including a seating unit 100 and a main body unit 200, and a discharge channel 210.

The seating unit 100 has a curved shape corresponding to a curvature of the genital area and buttocks of a human body, and has disposal spaces T1 and T2 which are opened in the direction of the genital area and buttocks and receive the excreta discharged from the human body.

Here, the genital area of the human body refers to an area around the sexual organ of the male and female, and the buttocks are connected to the above-mentioned genital area and refers to an area around the anus. That is, the seating unit 100 is formed to be seated in the groin of the human body, and has a curved shape corresponding to the curvature.

The disposal spaces T1 and T2 are formed to have a certain volume so as to receive excreta including urine and feces. The disposal spaces T1 and T2 of the present embodiment include an urine disposal unit T2 corresponding to the genital area of the human body and a feces disposal unit T1 corresponding to the buttocks of the human body.

That is, in the case of the present embodiment, the disposal spaces T1 and T2 are partitioned by a male module 300 so as to separately dispose of urine and feces. However, it is obvious that, in the case of using the excreta disposal apparatus 1 by a woman, unlike the present embodiment, a female module may be used instead of the male module 300. In the case of the female module, the urine disposal unit and the feces disposal unit may be connected without being partitioned. In addition, unlike the present embodiment, the male module 300 and the female module may be integrally formed without being separated.

The main body unit 200 is connected to the seating unit 100 so as to be mounted between the legs of the human body when a user wears the excreta disposal apparatus 1. That is, the user can stretch his/her legs to both sides of the main body unit 200 in a state in which the seating unit 100 is in close contact with the genital area and buttocks, so that the user can wear the excreta disposal apparatus 1.

In addition, although not shown in the drawing, a receiving space is provided inside the main body unit 200, and various elements may be provided in the receiving space. This will be described later.

Meanwhile, for convenience of explanation, the open direction side of the disposal spaces T1 and T2 is defined as a front side, and the opposite direction is defined as a rear side. Further, the direction in which the urine disposal unit T2 is provided is defined as an upper side and the opposite direction is defined as a lower side.

The discharge channel 210 is provided in the receiving space and communicates with the disposal spaces T1 and T2 to discharge the excreta of the disposal spaces T1 and T2 to the outside. Particularly, in the present embodiment, a through hole 202 is formed in the rear side of the main body unit 200 so that an external connection pipe can be inserted into the receiving space.

The connection pipe may include an excreta flow pipe connected to suck excreta by using a separate suction device, a cleaning water feeding pipe for supplying wash water, and the like. That is, the discharge channel 210 is connected to the excreta flow pipe so that the excreta can be discharged to the outside.

Figure 2:
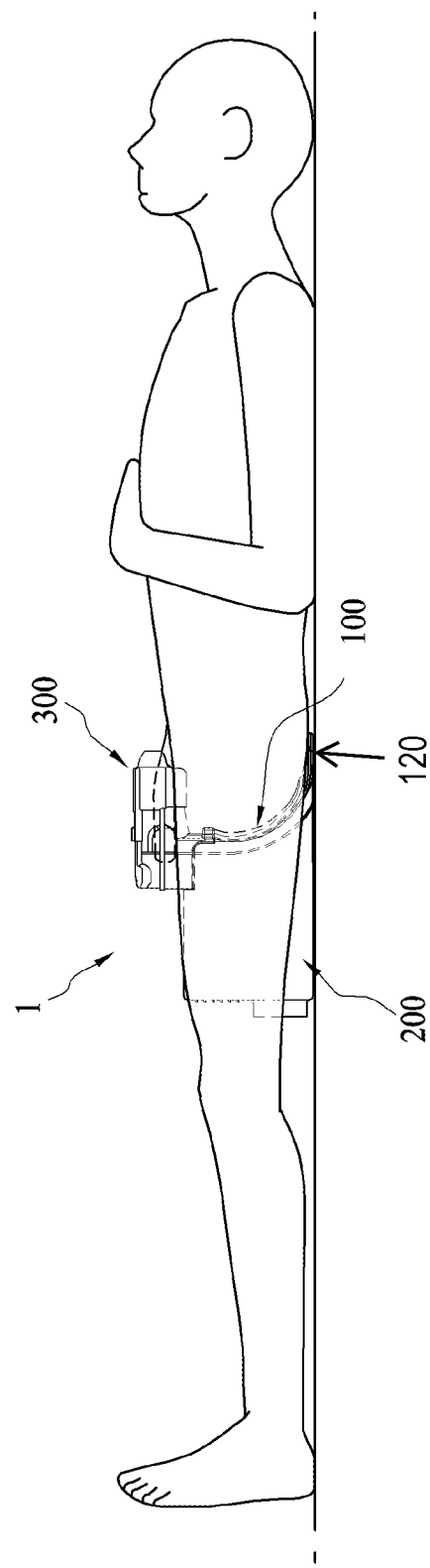
FIG. 2 is a side view of an excreta disposal apparatus worn on a human body according to an embodiment of the present invention.

FIG. 2 is a side view of an excreta disposal apparatus worn on a human body according to an embodiment of the present invention.

As shown in FIG. 2, the user adheres the seating unit 100 to the genital area and buttocks while lying on a bed or the like, and stretches legs on both sides of the main body unit 200 to stably wear the excreta disposal apparatus. As described above, since the excreta disposal apparatus 1 according to an embodiment of the present invention is formed to correspond to the shape of the human body, there is no need for the user to change the posture forcibly according to the excreta disposal apparatus 1.

In addition, even if the user changes his/her posture from side to side or the like, it can be moved along the user's body without being detached, and does not interfere with user's movement in a state of being positioned between the user's legs even when the user moves.

Figure 3:
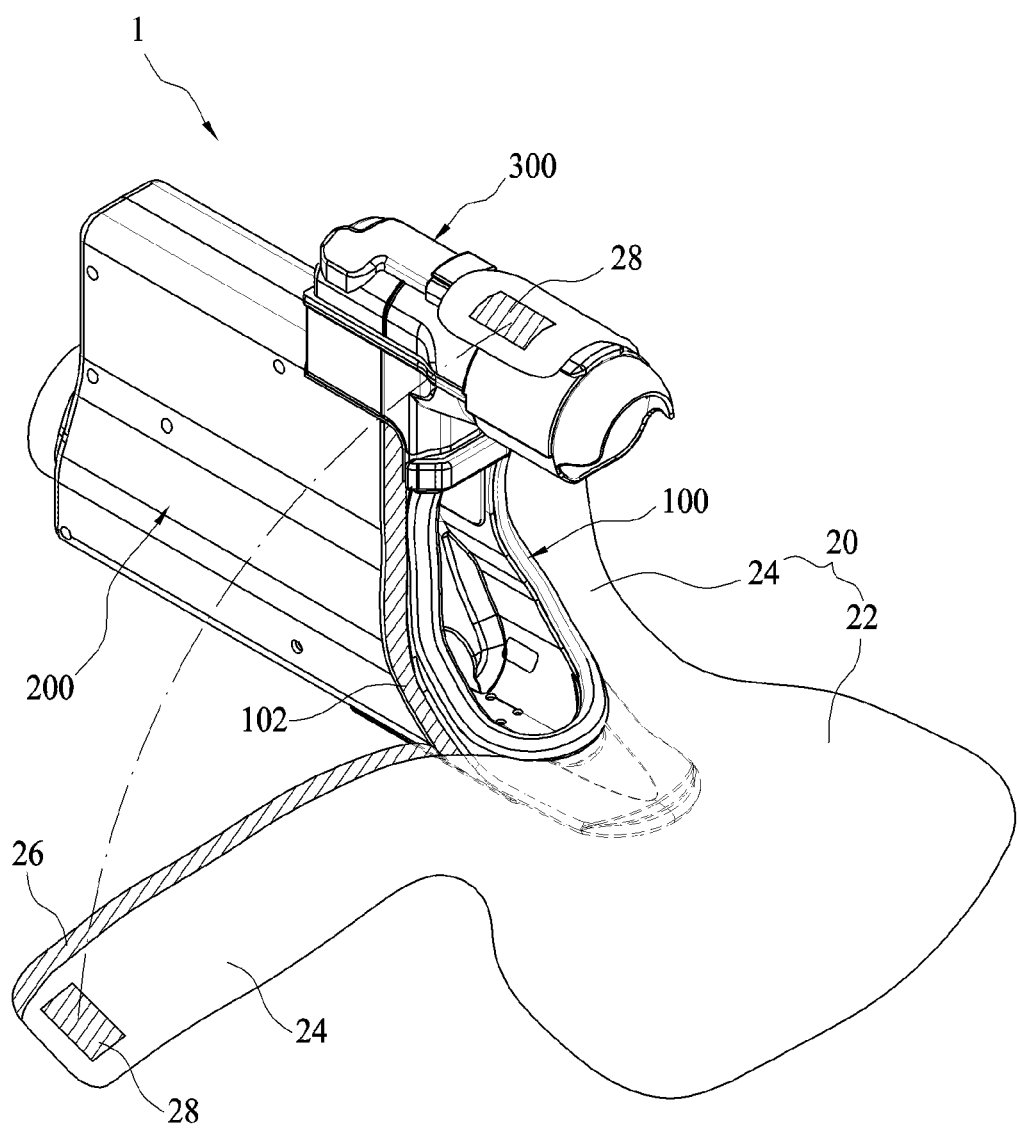
FIG. 3 is a perspective view showing a state where a pad is attached to a seating unit of an excreta disposal apparatus according to an embodiment of the present invention.

FIG. 3 is a perspective view showing a state where a pad 20 is attached to the seating unit 100 of the excreta disposal apparatus 1 according to an embodiment of the present invention.

As shown in FIG. 3, the excreta disposal apparatus 1 according to an embodiment of the present invention may include a pad 20 detachably installed to surround the seating unit 100. The pad 20 may be made of fabric or the like to improve the wearer's feeling of wearing, and may stably fix the excreta disposal apparatus 1 to the user's body.

In the case of the present embodiment, the pad 20 includes a pack portion 22 and a wing portion 24. The pack portion 22 is attached to the lower side of the seating unit 100 so as to surround the user's buttocks. The wing portion 24 is attached so as to surround the seating unit 100. Meanwhile, in order to attach the pad 20 to the seating unit 100, the seating unit 100 and the pad 20 may be provided with a velcro. That is, a seating unit velcro 102 and a pad velcro 26 are formed to correspond to each other, so that the pad 20 can be easily attached. In addition, in the present embodiment, each wing portion 24 is provided with a fixation velcro 28 so that respective wing portions 24 can be fixed to each other.

Figure 4:
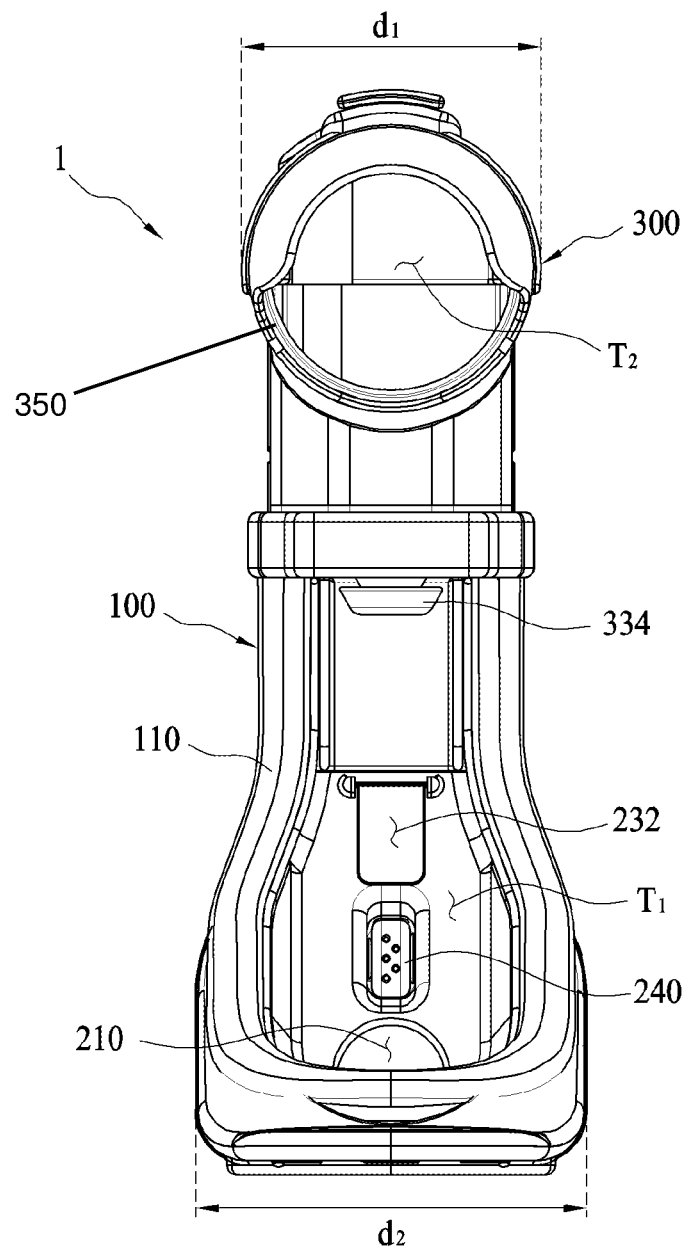
FIG. 4 is a front view of an excreta disposal apparatus according to an embodiment of the present invention.

FIG. 4 is a front view of the excreta disposal apparatus 1 according to an embodiment of the present invention.

FIG. 4 shows the disposal spaces T1 and T2 of the seating unit 100 in more detail. As described above, in the present embodiment, the disposal spaces T1 and T2 include the urine disposal unit T2 and the feces disposal unit T1. Various elements for disposing of the excreta may be provided in the disposal spaces T1 and T2.

A spraying portion is an element that is exposed to the disposal spaces T1 and T2 to spray washing water, and may include one or more spraying nozzles. In the case of the present embodiment, the spraying portion is provided with a rotary nozzle 240 for spraying washing water to the feces disposal unit T1 side, an auxiliary nozzle 334, and, although not shown, an upper side nozzle for spraying washing water to the urine disposal unit T2 side.

That is, the angle of the rotary nozzle 240 can be controlled to clean the periphery of the buttocks of the human body, and the auxiliary nozzle 334 sprays washing water so as to clean the surface of the feces disposal unit T1. In addition, the upper side nozzle also sprays washing water to clean the genital area and the surface of the urine disposal unit T2.

In addition, in the present embodiment, a drying air jet opening 232 is formed in the disposal space T1 and T2 to allow a drying air to flow and be jetted, thereby rapidly drying the water after cleaning.

Meanwhile, as shown in the drawing, the body including the seating unit 100 and the main body unit is formed in such a manner that a width d1 of the upper portion is narrower than a width d2 of the lower portion when viewed from the front. That is, it has a shape corresponding to the curved shape of a thigh portion of the human body, so that both legs of the user can be stably adhered to both sides of the body of the excreta disposal apparatus 1. In addition, the body is formed to have a width corresponding to the width between the legs of the user, so that the user can take a natural posture without opening his/her legs forcibly.

In the present embodiment, a fastening member 110 is provided around the seating unit 100 to be in close contact with the user's body. The fastening member 110 is provided in a band shape along the circumferential line of the seating unit 100, so that the feelings of wearing can be improved.

Figure 5:
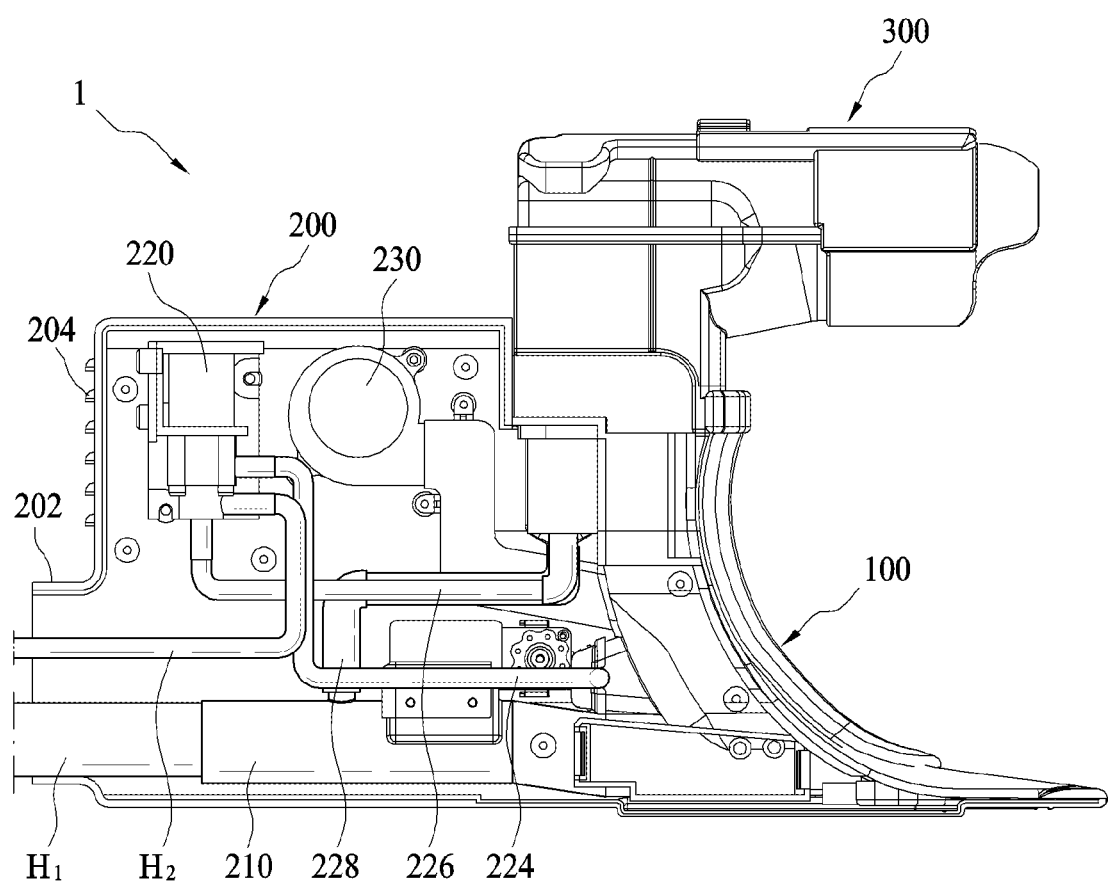
FIG. 5 is a cross-sectional view showing an internal structure of a main body in an excreta disposal apparatus according to an embodiment of the present invention.

FIG. 5 is a cross-sectional view showing an internal structure of the main body 200 in the excreta disposal apparatus 1 according to an embodiment of the present invention.

As shown in FIG. 5, a receiving space is formed inside the main body unit 200, and the receiving space may include various elements. In the present embodiment, the receiving space is provided with the above mentioned discharge channel 210, a flow channel switching unit 220, and an air blowing unit 230.

The discharge channel 210 is connected to an excreta flow tube H1 that is introduced through the through hole 202 to discharge the excreta to the outside. Particularly, in the present embodiment, the urine received from the male module 300 can be introduced into the discharge channel 210 through an auxiliary discharge channel 228.

The flow channel switching unit 220 is an element which is connected to a washing water feeding pipe H2 introduced through the through hole 202 and receives the washing water from the outside, and ramifies and supplies the washing water to a plurality of spray nozzles through a solenoid valve or the like.

Specifically, in the present embodiment, the washing water stored in the flow channel switching unit 220 may flow to the rotary nozzle through a first supply channel 224 and may flow to the auxiliary nozzle and the upper side nozzle through a second supply channel 226.

The air blowing unit 230 is an element which blows dry air to the disposal space, can generate dry air by using a blowing fan or the like, and can blow the dry air to the disposal space side through the drying air jet opening. Further, a heater may be further provided so as to increase the temperature of the dry air.

In the present embodiment, an air inlet 204 is formed on the rear surface of the main body unit 200 to allow an external air to flow to ventilate the inside of the receiving space.

Figure 6:
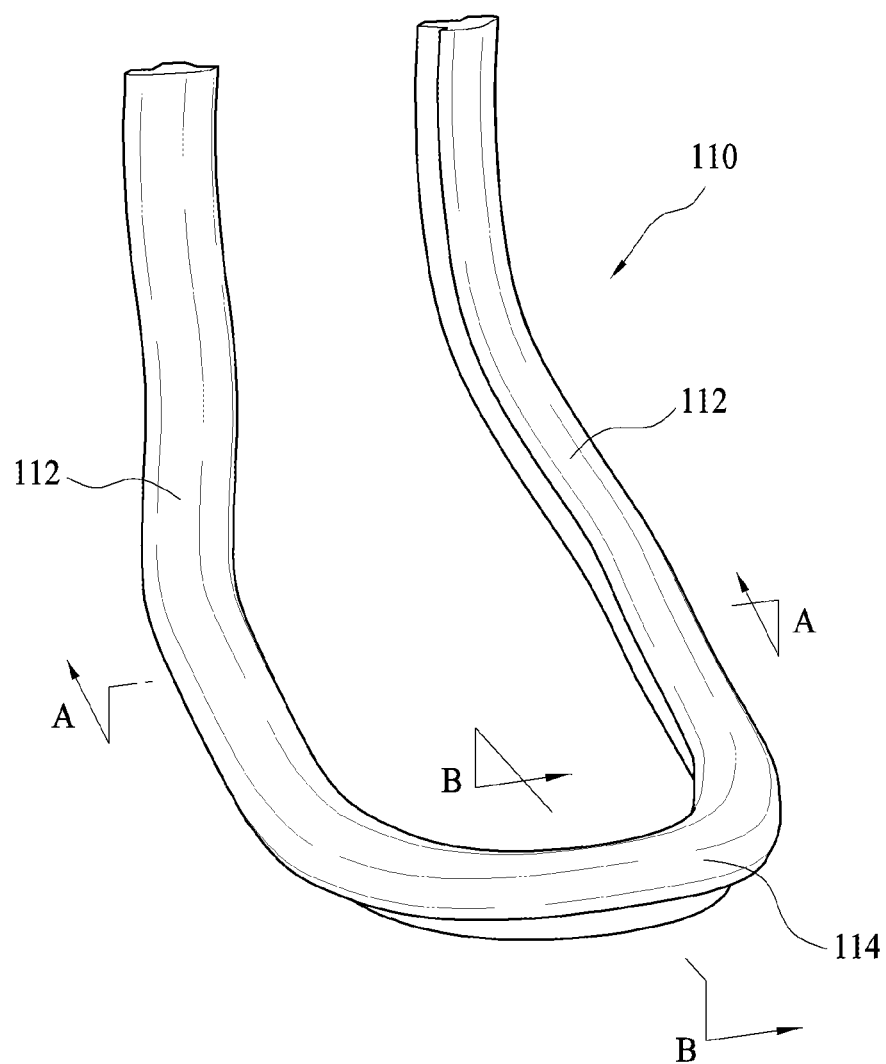
FIG. 6 is a perspective view showing a state of a fastening member in an excreta disposal apparatus according to an embodiment of the present invention.

FIG. 6 is a perspective view showing a state of the fastening member 110 in the excreta disposal apparatus according to an embodiment of the present invention.

As shown in FIG. 6, the present embodiment further includes the fastening member 110. The fastening member 110 is provided along the periphery of the seating unit so as to be in contact with the user's body, and has an inclination corresponding to the curvature inclination of the human body part. That is, since the fastening member 110 is formed to have an inclination similar to the curvature of the user's body, the fastening member 110 does not cause a foreign body sensation or pain when worn.

Meanwhile, since the disposal space in the present embodiment includes the feces disposal unit and the urine disposal unit, a plurality of fastening members 110, 350 (FIG. 4) may also be provided separately in the feces disposal unit and the urine disposal unit respectively.

In the case of FIG. 6, the fastening member 110 provided in the feces disposal unit is shown, and the fastening member provided in the urine disposal unit may be formed differently depending on the shape of the urine disposal unit.

The fastening member 110 includes a buttocks contact area 114 which contacts the user's buttocks and a thigh contact area which extends upward from both sides of the buttocks contact area 114 and contacts the inside of the user's thigh 112. That is, since the human body's buttocks and the inside of the thigh have a different inclination angle, each area is formed to have an inclination corresponding to a relevant part.

Figure 7:
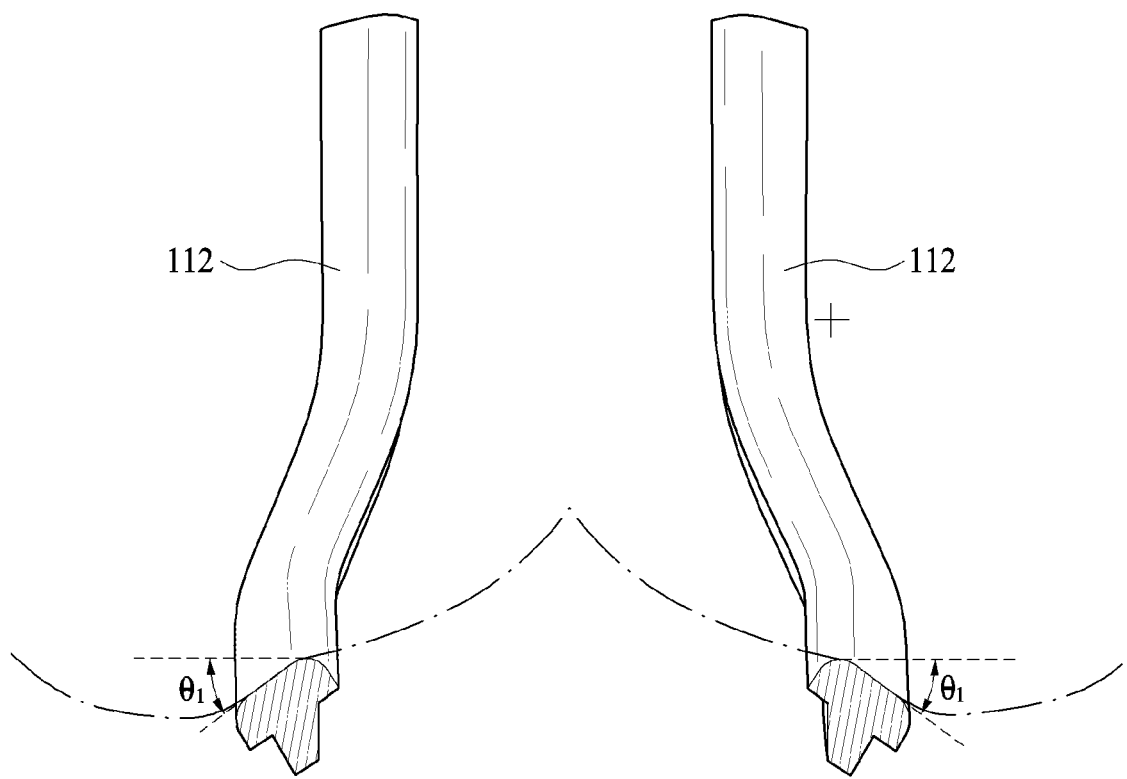
FIG. 7 is a cross-sectional view showing a cross section of a thigh contact area of a fastening member in an excreta disposal apparatus according to an embodiment of the present invention.

FIG. 7 is a cross-sectional view showing a cross section of the thigh contact area of the fastening member in the excreta disposal apparatus according to an embodiment of the present invention.

FIG. 7 shows a sectional view taken along the line A-A of FIG. 6, and may check the inclination of the thigh contact area 112. As shown in the drawing, the thigh contact area 112 may be formed in such a manner that a contact surface contacting the human body is inclined upwards in the direction in which the disposal space is formed. Therefore, the cross-section of the thigh contact area 112 has a shape inclined by a first angle θ1 from a horizontal line extended in the lateral direction.

Thus, the thigh contact area 112 shall be formed in a shape corresponding to the curved shape of the thigh of the user.

Figure 8:
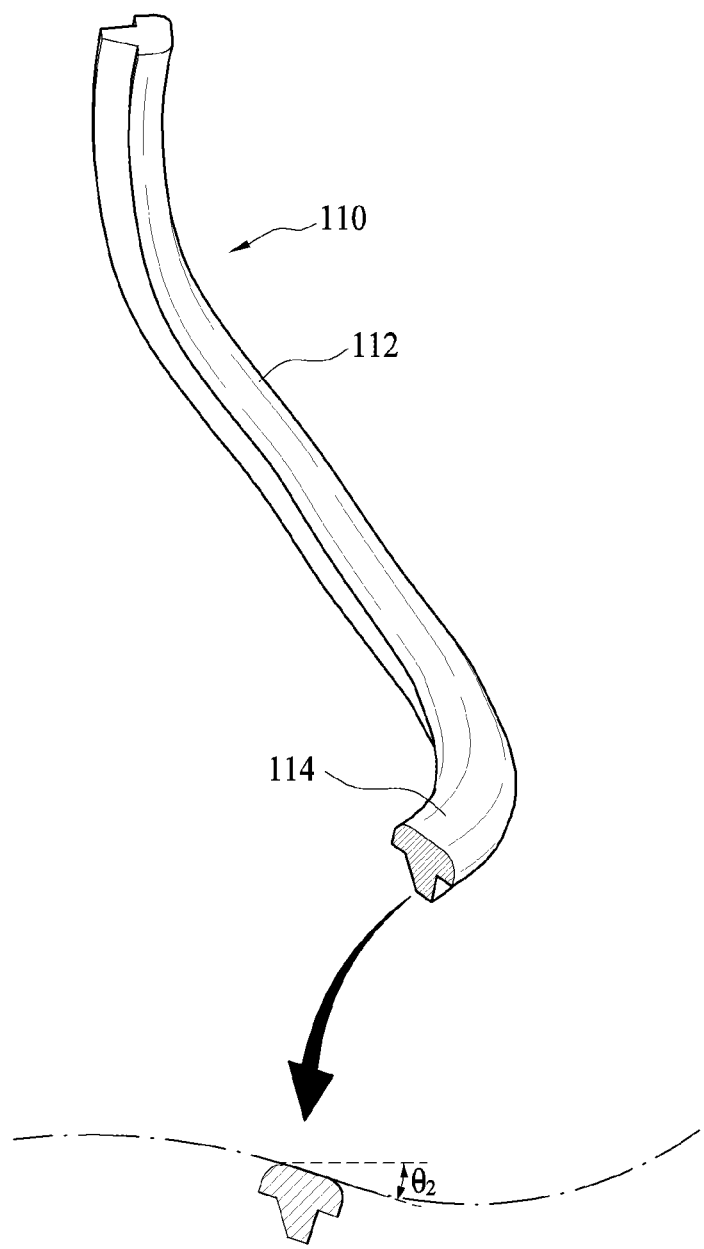
FIG. 8 is a cross-sectional view showing a section of a buttocks contact area of a fastening member in an excreta disposal apparatus according to an embodiment of the present invention.

FIG. 8 is a cross-sectional view showing a section of the buttocks contact area 114 of the fastening member in the excreta disposal apparatus according to an embodiment of the present invention.

FIG. 8 is a sectional view taken along the line B-B of FIG. 6, and the inclination of the buttocks contact area 114 can be checked. As shown in the drawing, the buttocks contact area 114 may be formed in such a manner that a contact surface contacting the human body is inclined upwards in the direction in which the disposal space is formed. Therefore, the cross section of the buttocks contact area 114 has a shape inclined by a second angle θ2 from a horizontal line extended in a forward-backward direction.

Thus, the buttocks contact area 114 shall be formed in a shape corresponding to the curved shape of the user's buttock.

Meanwhile, the fastening member 110 may be formed in such a manner that the inclination of the contact surface, which is in contact with the human body, decreases from the thigh contact area 112 to the buttocks contact area 114. That is, the fastening member 110 is formed to correspond to a curved line ranging from the thigh to the buttocks of the human body, thereby providing a comfortable feelings of wearing to the user.

Figure 9:
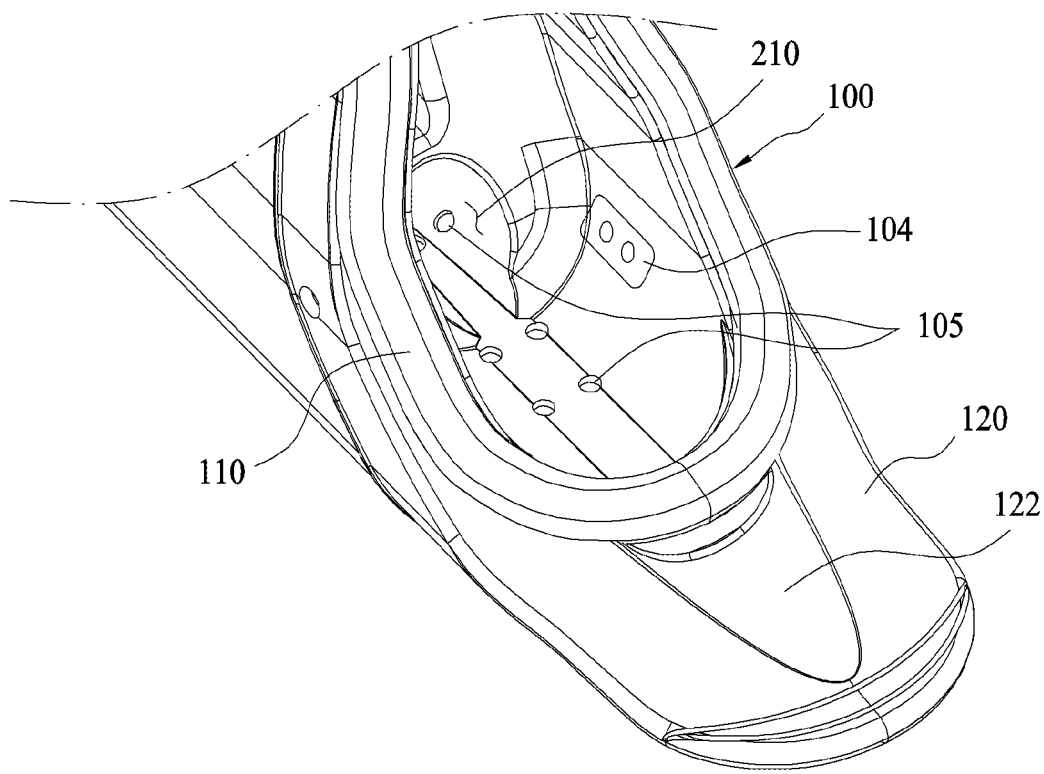
FIG. 9 is a perspective view showing an extension portion in an excreta disposal apparatus according to an embodiment of the present invention.

FIG. 9 is a perspective view showing an extension portion 120 in the excreta disposal apparatus according to an embodiment of the present invention.

As shown in FIG. 9, the excreta disposal apparatus according to an embodiment of the present invention further includes the extension portion 120 which is extended from the seating unit 100 and is configured to contact the buttocks of the human body.

The extension portion 120 is elongated in the direction of the buttocks of the human body, and thus, is formed to support the buttocks. Therefore, the user's feelings of wearing can be more improved and the excreta disposal apparatus can be more stably fixed to the human body.

In addition, as the extension portion 120 is formed, the seating unit 100 and the extension portion 120 are formed to entirely wrap around the curvature of the human body ranging from the genital area and buttocks of a human body so that it can be closely adhered to the human body so as not to leak the internal excreta to the outside.

In the present embodiment, in the extension portion 120, a recessed groove 122 is formed in a position corresponding to a coccyx of the human body. The recessed groove 122 is formed in a recessed shape so as to prevent the protruded coccyx from being pressed by the surface of the extension portion when the user puts the buttocks on the extension portion 120, so that the user can feel a comfortable feelings of wearing.

Meanwhile, as shown in the drawing, a detection sensor including a feces detection sensor 104 and an urine detection sensor 105 is provided in the disposal space to sense the existing of excreta, and to control each element when it is determined that excretion exists. In the present embodiment, the feces detection sensor 104 is located in both sides of the feces disposal space, and the urine detection sensor 105 is provided in the bottom of the feces disposal space and the discharge channel 210.

Figure 10:
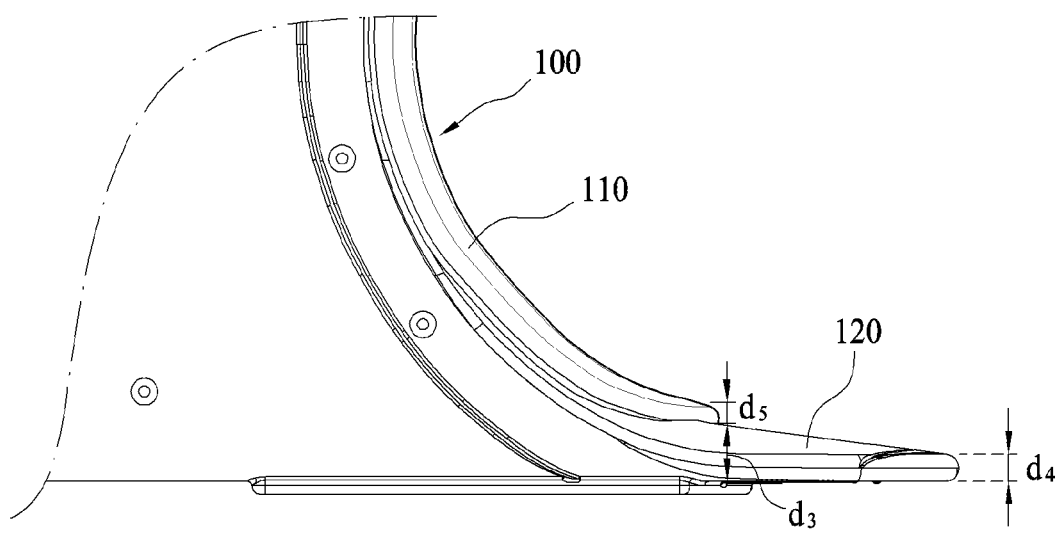
FIG. 10 is a side view showing a state of an extension portion in an excreta disposal apparatus according to an embodiment of the present invention.

FIG. 10 is a side view showing a state of the extension portion 120 in the excreta disposal apparatus according to an embodiment of the present invention.

As shown in FIG. 10, it can be seen that the seating unit 100 and the extension portion 120 are formed in a natural curved shape corresponding to the curved shape of the human body as a whole when viewed from the side.

At this time, the extension portion 120 is formed in such a manner that the height decreases when progressing from the rear side to the front side. That is, the height d3 of the rear side of the extension portion 120 is formed to be higher than the height d4 of the front side, and the extension portion 120 is formed to be inclined so that the height gradually decreases when progressing from the rear side to the front side. Further, the extension portion 120 is formed in such a manner that the height decreases when progressing from the center to the side.

Accordingly, when placing user's buttocks on the extension portion 120, the user does not feel a foreign body sensation and can be adhered to a cleaved portion of the buttocks so that the user can feel a comfortable feelings of wearing.

Meanwhile, in the present embodiment, the fastening member 110 is formed to be stepped from the rear side of the extension portion 120 by a certain height d5. This is to prevent the fastening member 110 and the pad from being stepped when the pad is attached to the periphery of the seating unit 100, so that the height d5 of the step may correspond to the thickness of the pad.

As described above, in the excreta disposal apparatus of the present invention, the seating unit is formed to correspond to the curvature of the genital area and buttocks of the user, and the main body unit has a size corresponding to the width between the legs of the user. Accordingly, it is possible to naturally maintain the posture of the user, to improve the feelings of wearing, and to prevent the leak of excreta.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims. Accordingly, the scope of the present invention is not construed as being limited to the described embodiments but is defined by the appended claims as well as equivalents thereto.

The invention claimed is:

1. An excreta disposal apparatus customized to a human body, the apparatus comprising:
 a body comprising
  a seating unit, which has a shape corresponding to a curved shape of a genital area and buttocks of the human body and also has a disposal space open toward the genital area and buttocks of the human body so as to take excreta discharged from the human body, the disposal space comprising a feces disposal unit corresponding to a hip of a human body,
  a main body unit, which is connected to the seating unit so as to be mounted between legs of the human body and has a receiving space therein,
  and an extension portion extending from the seating unit and configured to support the buttocks of the human body, the extension portion being configured to be adhered to a cleaved portion of the buttocks of the human body, and has a height that is decreased when progressing from a rear side to a front side and is decreased when progressing from a center to a side thereof;
 a urine disposal unit corresponding to the genital area of the human body configured to receive and discharge urine into an auxiliary discharge channel;
 a discharge channel, which is provided in the receiving space and communicates with the disposal space and the auxiliary discharge channel so as to discharge the excreta in the disposal space and the urine in the urine disposal unit through an excreta flow tube to an outside of the disposal space;
 a fastening member which is provided around the seating unit and adapted to be in contact with a user's body at one or more contact areas, and each contact area has an inclination corresponding to a curvature inclination of a corresponding human body part; and
 a pad detachably attached to surround a periphery of the seating unit, wherein the fastening member is formed to be stepped by a predetermined height corresponding to a thickness of the pad from the rear side of the extension portion.

2. The apparatus of claim 1, wherein the disposal space comprises the urine disposal unit.

3. The apparatus of claim 1, wherein the extension portion is formed in such a manner that a recessed groove is formed in a position corresponding to a coccyx of the human body.

4. The apparatus of claim 1, wherein a width of an upper portion of the body is narrower than a width of a lower portion of the body.

5. The apparatus of claim 1, wherein a through hole is formed in a rear side of the main body unit so that at least one of the excreta flow tube or a washing water feed pipe can be inserted into the receiving space.

6. The apparatus of claim 1, further comprising a spraying portion exposed to the disposal space and configured to spray washing water.

7. The apparatus of claim 6, further comprising a flow channel switching unit provided in the receiving space and configured to supply washing water from a washing water feed pipe to the spraying portion via a solenoid valve.

8. The apparatus of claim 1, further comprising an air blowing unit provided in the receiving space and configured to blow dry air to the disposal space.

9. The apparatus of claim 1, further comprising a detection sensor provided in the disposal space and configured to detect excreta.

10. The apparatus of claim 1, wherein the fastening member is comprised of a first part and a second part, the first part attached to the feces disposal unit and the second part attached to the urine disposal unit.

11. The apparatus of claim 1, wherein the one or more contact areas comprise:
 a buttocks contact area adapted for contact with user's buttocks; and
 a thigh contact area extending from both sides of the buttocks contact area and adapted for contact with the inside of user's thigh.

12. The apparatus of claim 11, wherein the buttocks contact area has a buttocks contact surface adapted for contacting the human body.

13. The apparatus of claim 11, wherein the thigh contact area has a thigh contact surface adapted for contacting the human body.

* * * * *